United States Patent [19]
Backus et al.

[11] Patent Number: 6,001,558
[45] Date of Patent: Dec. 14, 1999

[54] AMPLIFICATION AND DETECTION OF HIV-1 AND/OR HIV 2

[75] Inventors: John W. Backus, San Diego, Calif.; Susan M. Atwood; Ann E. Casey, both of Rochester, N.Y.; Eric B. Rasmussen, Madison, Wis.; Thomas J. Cummins, Penfield, N.Y.

[73] Assignee: Ortho Clinical Diagnostics, Inc., Rochester, N.Y.

[21] Appl. No.: 09/102,830

[22] Filed: Jun. 23, 1998

Related U.S. Application Data

[60] Provisional application No. 60/050,759, Jun. 25, 1997, abandoned.

[51] Int. Cl.⁶ ..................................................... C12Q 1/68
[52] U.S. Cl. ........................... 435/5; 435/91.1; 435/91.2; 435/6
[58] Field of Search ................................... 435/5, 6, 91.1, 435/91.2; 935/77, 78

[56] References Cited

U.S. PATENT DOCUMENTS 5,795,722  8/1998  Lacroix et al. ............................ 435/6

FOREIGN PATENT DOCUMENTS

WO 91/08308  6/1991  WIPO .

*Primary Examiner*—Ardin H. Marschel

[57] ABSTRACT

The present invention relates to methods and test kits for the amplification and detection of nucleic acids from human immunodeficiency virus (HIV) type 1 and/or type 2. The methods use multiple primer sets to amplify all subtypes of HIV-1, including group M and group O isolates, and all subtypes of HIV-2.

14 Claims, No Drawings

6,001,558

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

GACCAGATCT GAGCCTGGGA GCT                                                  23

(2) INFORMATION FOR SEQ ID NO:2:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

CTGCTTAAGC CTCAATAAAG CTTGCCTTGA                                           30

(2) INFORMATION FOR SEQ ID NO:3:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

GGGTCTGAGG GATCTCTAGT TACCAGAGT                                            29

(2) INFORMATION FOR SEQ ID NO:4:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

TGTTCGGGCG CCACTGCTAG AGA                                                  23

(2) INFORMATION FOR SEQ ID NO:5:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:5:

```
CAACAGACGG GCACACACTA CT                                                  22

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GAACAGATGG GCACACACTG CT                                                  22

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TCGGGTTTAT TACAGGGACA GCAGAGA                                             27

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CTTGTATTAC TACTGCCCCT TCACCTTTCC A                                        31

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AGCTTTGCTG GTCCTTTCCA AAGTGGG                                             27

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AGTTGTGCCG GTCCTTTCCA AATTGGG                                             27

(2) INFORMATION FOR SEQ ID NO:11:
```

```
    (i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CCGGGATAGT GCAGCAACAG CAACA                                               25

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CCCAGACGGT CAGTCGCAAC A                                                   21

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TGGACGTGGT CAAGAGACAA CAAGAA                                              26

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GGGAGGTTCT CTCCAGCACT AGCA                                                24

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GAGCCCTGGG AGGTTCTCTC CA                                                  22

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:16:

GCGACTAGGA GAGATGGGAA CACACA                                    26

(2) INFORMATION FOR SEQ ID NO:17:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:17:

CCACGCTTGC TTGCTTAAAG ACCTC                                     25

(2) INFORMATION FOR SEQ ID NO:18:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:18:

TAGACACAGG GGCTGACGAC TCAATAGT                                  28

(2) INFORMATION FOR SEQ ID NO:19:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:19:

CACAGGGGCT GACGACTCAA TAGTAGCA                                  28

(2) INFORMATION FOR SEQ ID NO:20:

(i) SEQUENCE CHARACTERISTICS:
       (A) LENGTH: 35 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:20:

GCCAAAAATG TTGATTGGGG TATCTCCTGT CATTA                          35

(2) INFORMATION FOR SEQ ID NO:21:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:21:

```
CCAAAAATAG TAGGGGGAAT AGGGGGATTC                                    30

(2) INFORMATION FOR SEQ ID NO:22:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CACCCCAAAA ATAGTAGGTG GGATAGGAGG G                                  31

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GACCAGATCT GAGCCTGGGA GCTC                                          24

(2) INFORMATION FOR SEQ ID NO:24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CTGCTTAAGC CTCAATAAAG CTTGCCTTGA G                                  31

(2) INFORMATION FOR SEQ ID NO:25:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GGTCTGAGGG ATCTCTAGTT ACCAGAGT                                      28

(2) INFORMATION FOR SEQ ID NO:26:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

GGGTCTGAGG GATCTCTAGT TACCAG                                        26

(2) INFORMATION FOR SEQ ID NO:27:
```

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GTATTACTAC TGCCCCTTCA CCTTTCCA                                           28

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CGGGATAGTG CAGCAACAGC AACAG                                              25

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CCCCAGACGG TCAGTCGCAA CA                                                 22

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CCCTGGGAGG TTCTCTCCAG CA                                                 22

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

CTGTTCGGGC GCCAACCTGC TA                                                 22

(2) INFORMATION FOR SEQ ID NO:32:

(i) SEQUENCE CHARACTERISTICS:
        (A) LENGTH: 35 base pairs
        (B) TYPE: nucleic acid
        (C) STRANDEDNESS: single
        (D) TOPOLOGY: linear

```
        (ii) MOLECULE TYPE: DNA (genomic)

(xi) SEQUENCE DESCRIPTION: SEQ ID NO:32:

CTGCACCTCA ATTCTCTCTT TGGAAAAGAC CAGTA                                35

(2) INFORMATION FOR SEQ ID NO:33:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:33:

GCACCTCAAT TCTCTCTTTG GAAAAGACCA GTA                                  33

(2) INFORMATION FOR SEQ ID NO:34:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:34:

GCCAAAAATG TTGATTGGGG TATCTCCTGT CA                                   32
```

AMPLIFICATION AND DETECTION OF HIV-1 AND/OR HIV 2

This application claims the benefit of U.S. Provisional Application No. 60/050,759, filed on Jun. 25, 1997, now abandoned.

BACKGROUND OF THE INVENTION

1. Field of the Invention

The present invention relates to methods and test kits for the amplification and detection of human immunodeficiency virus (HIV). In particular, the present invention relates to PCR methods that use multiple primer sets to amplify all subtypes of HIV-1, including group M and group O isolates, and all subtypes of HIV-2.

2. Background Information

Progress has been made in our understanding of acquired immunodeficiency syndrome (AIDS) and its causative agent, the human immunodeficiency virus (HIV). Two groups of human immunodeficiency viruses, HIV-1 and HIV-2, have been identified. HIV-1 and HIV-2 are genetically related, but are nevertheless distinct. Both HIV-1 and HIV-2 show considerable genetic variability among their different isolates. Indeed, ten subtypes of HIV-1 (group M comprising subtypes A to I and group O comprising subtype O) have been identified. While consensus sequences have been generated for HIV-1 and HIV-2 from published nucleotide sequences of various HIV-1 and HIV-2 isolates, it is impossible to find substantial regions of absolute sequence conservation between all isolates of HIV-1 or all isolates of HIV-2. In addition to the genetic variability found among HIV isolates, many nucleotide regions of HIV are as highly conserved between HIV and non-related viruses as they are within the HIV-1 and HIV-2 families. These facts, taken together, make it extremely difficult to design polymerase chain reaction (PCR) primers and probes that will efficiently detect all group M and group O subtypes of HIV-1 and all HIV-2 subtypes without falsely detecting non-related viruses.

One of the challenges facing those attempting to develop amplification systems that detect all known HIV-1 and HIV-2 subtypes is the development of oligonucleotide primer sets which perform adequately when used together under a single set of amplification conditions (such as, salt conditions, temperatures, and amplification times). Identifying primers and detection probes that are compatible in terms of primer-primer and primer-probe interactions is an even greater challenge. Thus, in the case of the amplification and detection of HIV-1 and/or HIV-2, steps maximizing the probability of detecting highly divergent subtypes or isolates under less than ideal conditions are still needed.

SUMMARY OF THE INVENTION

The present invention overcomes the above-noted problems and provides a needed means of amplifying and detecting highly divergent HIV-1 and/or HIV-2 isolates. Thus, it is an object of the present invention to provide methods and test kits for the detection of all known HIV-1 subtypes and/or HIV-2 subtypes.

Various other objects and advantages of the present invention will be apparent from the detailed description of the invention.

In one embodiment, the present invention relates to a method for amplifying HIV-1 nucleic acids. The method comprises contacting Ad a sample suspected of containing HIV-1 nucleic acids with four different nucleoside triphosphates, a thermostable DNA polymerase, and at least four oligonucleotides, under conditions such that HIV-1 target nucleic acid is amplified. The four oligonucleotides are selected from the sets:

(a) SEQ ID NOS.: 1, 3, 7, and 8;
(b) SEQ ID NOS.: 1, 4, 7, and 8;
(c) SEQ ID NOS.: 2, 3, 7, and 8; and
(d) SEQ ID NOS.: 2, 4, 7, and 8.

In another embodiment, the present invention relates to a method for amplifying HIV-2 that comprises contacting a sample with four different nucleoside triphosphates, a thermostable DNA polymerase, and at least four oligonucleotides, under conditions such that HIV-2 target nucleic acid is amplified. The four oligonucleotides are selected from the sets:

(a) SEQ ID NOS.: 11, 12, 14, and 16;
(b) SEQ ID NOS.: 11, 12, 15, and 16;
(c) SEQ ID NOS.: 11, 12, 18, and 20;
1(d) SEQ ID NOS.: 11, 12, 19, and 20;
(e) SEQ ID NOS.: 14, 16, 18, and 20;
(f) SEQ ID NOS.: 14, 16, 19, and 20;
(g) SEQ ID NOS.: 15, 16, 18, and 20; and
(h) SEQ ID NOS.: 15, 16, 19, and 20.

In a further embodiment, the present invention relates to a method for coamplifying HIV-1 and HIV-2 target nucleic acid. A sample suspected of containing any HIV nucleic acid is contacted with four different nucleoside triphosphates, a thermostable DNA polymerase, at least one primer pair selected from SEQ ID NOS. 1, 2, 3, 4, 7, and 8 and at least one primer pair selected from SEQ ID NOS. 11, 12, 14, 15, 16, 18, 19 and 20, under conditions such that target HIV-1 and HIV-2 nucleic acids are amplified.

All publications mentioned herein are hereby incorporated by reference.

DETAILED DESCRIPTION OF THE INVENTION

The development of a co-amplification system for HIV-1 and HIV-2 that can sensitively and specifically detect all subtypes of HIV-1 and HIV-2 is an extreme challenge for several reasons: (1) the diversity at the nucleic acid sequence level between individual isolates, (2) the need to minimize primer-primer interactions between at least 8–10 primers, as side product formation will reduce assay sensitivity and also possibly specificity, (3) the need to specifically detect the amplified products, which ideally should be done by oligonucleotide hybridization with a probe internal to the amplification primers and (4) the need to control for both the presence of inhibitors in prepared patient specimens and also inefficient recovery of target nucleic acid from sample preparation. Applicants have overcome these obstacles and arrived at the present invention relating to the amplification and/or detection of HIV-1 and HIV-2 nucleic acids.

In the present invention, primer sets have been developed for HIV-1 and HIV-2 that are compatible with each other and can, therefore, be combined to form a complex co-amplification assay that can detect all sequenced isolates of HIV-1 and HIV-2. With the methods of the present invention, those skilled in the art are able to sensitively and specifically amplify and detect both HIV-1 and HIV-2 target nucleic acids with a high level of confidence. This amplification and detection can be carried out in a multiplexed fashion and in the presence of an internal positive control (IPC) that signals false negative results due to problems in sample preparation, amplification and/or detection.

The present invention relates to methods for amplifying HIV-1 and/or HIV-2 nucleic acids. Oligonucleotide primer sets have been identified, which when used in various combinations, sensitively and specifically amplify target nucleic acids from all known isolates of HIV-1 and/or HIV-2. To amplify HIV-1 target nucleic acids according to the present invention, primer sets are selected from the following oligonucleotides:

```
HIV-1
LTR Region Primers:

GACCAGATCTGAGCCTGGGAGCT (SEQ ID NO. 1)

CTGCTTAAGCCTCAATAAAGCTTGCCTTGA (SEQ ID NO. 2)

GGGTCTGAGGGATCTCTAGTTACCAGAGT (SEQ ID NO. 3)

TGTTCGGGCGCCACTGCTAGAGA (SEQ ID NO. 4)

POL Region Primers:

TCGGGTTTATTACAGGGACAGCAGAGA (SEQ ID NO. 7)

CTTGTATTACTACTGCCCCTTCACCTTTCCA (SEQ ID NO. 8)
```

In the methods of the present invention, HIV-1 target nucleic acid is amplified by contacting a biological sample suspected of containing HIV nucleic acids with a primer set comprising at least four oligonucleotides. Primer sets suitable for use in the present invention include, but are not limited to (a) SEQ ID NOS.: 1, 3, 7, and 8;
(b) SEQ ID NOS.: 1, 4, 7, and 8;
(c) SEQ ID NOS.: 2, 3, 7, and 8; and
(d) SEQ ID NOS.: 2, 4, 7, and 8.

The four oligonucleotides of these primer sets, may be used alone or in combination with other HIV-1 or HIV-2 primers. For example, oligonucleotide SEQ ID NO. 2 could be used in connection with the primer sets (a) or (b) above. Preferred primer sets are:

(a) SEQ ID NOS.: 1, 2, 3, 7, and 8;
(b) SEQ ID NOS.: 1, 2, 4, 7, and 8;
(c) SEQ ID NOS.: 2, 3, 4, 7, and 8;
(d) SEQ ID NOS.: 1, 3, 4, 7, and 8; and
(e) SEQ ID NOS.: 1, 2, 3, 4, 7, and 8.

More preferred is the primer set containing oligonucleotides corresponding to SEQ ID NOS.: 2, 3, 4, 7, and 8. Any of these primer sets can be used to amplify nucleic acid from all known HIV-1 subtypes, including group M and group O.

In addition to the primer set(s) the biological sample is also contacted with PCR reagents, such as four different nucleoside triphosphates and a thermostable DNA polymerase, under conditions such that any HIV-1 nucleic acid present in the sample will be amplified.

To amplify HIV-2 target nucleic acid according to the present invention, primer sets are selected from the following oligonucleotides:

```
HIV-2
ENV Region Primers:

CCGGGATAGTGCAGCAACAGCAACA (SEQ ID NO. 11)

CCCAGACGGTCAGTCGCAACA (SEQ ID NO. 12)

LTR Region Primers:

GGGAGGTTCTCTCCAGCACTAGCA (SEQ ID NO. 14)

GAGCCCTGGGAGGTTCTCTCCA (SEQ ID NO. 15)

GCGACTAGGAGAGATGGGAACACACA (SEQ ID NO. 16)

POL Region Primers:

TAGACACAGGGGCTGACGACTCAATAGT (SEQ ID NO. 18)

CACAGGGGCTGACGACTCAATAGTAGCA (SEQ ID NO. 19)

GCCAAAAATGTTGATTGGGGTATCTCCTGTCATTA (SEQ ID NO. 20)
```

In the methods of the present invention, HIV-2 target nucleic acid is amplified by contacting a biological sample suspected of containing HIV-2 nucleic acid with a primer set comprising at least four oligonucleotides. Primer sets suitable for use in the present invention include but are not limited to, (a) SEQ ID NOS.: 11, 12, 14, and 16;
(b) SEQ ID NOS.: 11, 12, 15, and 16;
(c) SEQ ID NOS.: 11, 12, 18, and 20;
(d) SEQ ID NOS.: 11, 12, 19, and 20;
(e) SEQ ID NOS.: 14, 16, 18, and 20;
(f) SEQ ID NOS.: 14, 16, 19, and 20;
(g) SEQ ID NOS.: 15, 16, 18, and 20;
(h) SEQ ID NOS.: 15, 16, 19, and 20.

Preferred is the primer set containing oligonucleotides corresponding to SEQ ID NOS.: 11, 12, 14 and 16. Any of these primer sets can be used to amplify nucleic acid from all known HIV-2 subtypes.

In addition to the primer set(s) the biological sample is also contacted with PCR reagents, such as four different nucleoside triphosphates and thermostable DNA polymerase, under conditions such that any HIV-2 target nucleic acid present in sample will be amplified.

To amplify both HIV-1 and HIV-2, a biological sample is contact ed with an HIV-1 primer set of th e present invention together with an HIV-2 primer set of the present invention. Preferably, the biological sample is contacted with oligonucleotides corresponding to SEQ ID NOS.: 2, 3, 4, 7, 8, 11, 12, 14, and 16. Use of such a set of primers can amplify target nucleic acid of any known HIV-1 and/or HIV-2 subtype present in the sample.

The methods of the present invention utilize, in some cases, more than two primers to amplify target nucleic acid sequences which overlap a common probe region such as a primer set including SEQ ID NOS.: 2, 3, and 4. This maximizes strain sensitivity and robustness of the amplification system. This novel feature increases strain sensitivity of the assay system and allows for the combination of primers which each have separate benefits, such as greater amplification efficiency and higher sequence homology among isolates, in effect increasing the sensitivity and robustness of the amplification system.

Once the HIV-1 and/or HIV-2 target is amplified using primer set(s) of the present invention, the presence or absence of the amplified HIV target can be detected using known detection methods. For example, the amplified target nucleic acid can be detected using one or more oligonucleotide probes specific for the amplified HIV-1 or HIV-2 target nucleic acid. Those skilled in the art can readily identify oligonucleotide probes that would be suitable to detect the amplified HIV-1 and/or HIV-2 target nucleic acid depending on the primer sets used. Oligonucleotide probes suitable for use in the present invention include, but are not limited to the following oligonucleotides:

```
HIV-1
LTR Region Probes:

CAACAGACGGGCACACACTACT (SEQ ID NO. 5)

GAACAGATGGGCACACACTGCT (SEQ ID NO. 6)

POL Region Probes:

AGCTTTGCTGGTCCTTTCCAAAGTGGG (SEQ ID NO. 9)

AGTTGTGCCGGTCCTTTCCAAATTGGG (SEQ ID NO. 10)

HIV-2
ENV Region Probe:

TGGACGTGGTCAAGAGACAACAAGAA (SEQ ID NO. 13)

LTR Region Probe:

CCACGCTTGCTTGCTTAAAGACCTC (SEQ ID NO. 17)

POL Region Probes:

CCAAAAATAGTAGGGGGAATAGGGGGATTC (SEQ ID NO. 21)

CACCCCAAAAATAGTAGGTGGGATAGGAGGG (SEQ ID NO. 22)
```

Preferably, the amplified HIV-1 and HIV-2 targets are detected using probes corresponding to SEQ ID NOS.: 5, 6, 9, and 10, with any of the following combinations: SEQ ID NOS. 13 and 17, or 13 and 22 or 17, 21 and 22.

The present invention uses multiple overlapping probes to detect all known isolates when probing in regions that have a low degree of sequence conservation relative to the primer regions. This allows amplification primers to be designed in regions which are not separated by a highly conserved and highly specific probe region typically required for sequence specific detection of the amplification product. In some situations, such as with HIV-1, multiple probes are necessary to detect all known isolates with high sensitivity.

The general principles and conditions for amplification and detection of nucleic acids using PCR are quite well known, the details of which are provided in numerous references, including U.S. Pat. No. 4,683,195 (Mullis et al.), U.S. Pat. No. 4,683,202 (Mullis), and U.S. Pat. No. 4,965,188 (Mullis et al.), all of which are incorporated herein by reference. Thus, in view of the teachings in the art and the specific teachings provided herein, a worker skilled in the art should have no difficulty in practicing the present invention to detect all known subtypes of HIV-1 and HIV-2.

The term "biological sample" includes, but is not limited to, cellular or viral material, hair, body fluids or cellular material containing nucleic acids that can be detected.

The term "oligonucleotide" refers to a molecule comprised of one or more deoxyribonucleotides or ribonucleotides, such as primers, probes, and nucleic acid fragments to be detected.

The term "primer" refers to an oligonucleotide, whether naturally occurring or synthetically produced, that is capable of acting as a point of initiation of synthesis when placed under conditions in which synthesis of a primer extension product complementary to a nucleic acid strand (that is, template) is induced, such conditions include the presence of other PCR reagents, and suitable temperature and pH.

The primer is preferably single stranded for maximum efficiency in amplification, but can contain a double stranded region if desired. It must be long enough to prime the synthesis of extension products in the presence of the DNA polymerase. The exact size of each primer will vary depending upon the use contemplated, the concentration and sequence of the primer, the complexity of the targeted sequence, the reaction temperature, and the source of the primer. Generally, the primers used in this invention will have from 12 to 60 nucleotides, and preferably, they have from 16 to 40 nucleotides. More preferably, each primer has from 18 to 35 nucleotides.

Primers useful herein can be prepared using known techniques and equipment, including for example an ABI DNA Synthesizer (available from Applied Biosystems) or a Biosearch 8600 Series or 8800 Series Synthesizer (available from Milligen-Biosearch, Inc.). Procedures for using this equipment are well known and described for example in U.S. Pat. No. 4,965,188 (Gelfand et al.), incorporated herein by reference. Naturally occurring primers isolated from biological sources may also be useful (such as restriction endonuclease digests). A set of at least two primers is generally used for each target nucleic acid. Thus, a plurality of sets of primers can be used simultaneously to amplify a plurality of target nucleic acids.

As used herein, a "probe" is an oligonucleotide which is substantially complementary to a nucleic acid sequence of the target nucleic acid and which is used for detection or capture of the amplified target nucleic acid.

In the present invention, sequence specific primers and probes are provided. It will be apparent to those skilled in the art that additional sequence specific primers and probes can be prepared by, for example, the addition of nucleotides to either the 5' or 3' ends, which nucleotides are complementary or noncomplementary to the target sequence. Such compositions are within the scope of this invention.

The primers and/or the probes used in the present invention can, optionally, be labeled. Using known methods in the art, the primers and/or probes can be labeled with a specific binding ligand (such as biotin), an enzyme (such as glucose oxidase, peroxidases, uricase, and alkaline phosphatase), radioisotopes, electron-dense reagents, chromogens, fluorogens, phosphorescent moieties or ferritin. Preferably, the label is a specific binding ligand. More preferably, the label is biotin or a derivative thereof, streptayidin or a derivative thereof, or a hapten.

A "PCR reagent" refers to any of the reagents considered essential for PCR, namely a set of primers for each target nucleic acid, a DNA polymerase, a DNA polymerase cofactor, and one or more deoxyribonucleoside-5'-triphosphates (dNTP's). Other optional reagents and materials used in PCR are described below. These reagents can be provided individually, as part of a test kit, or in reagent chambers of test devices.

A DNA polymerase is an enzyme that will add deoxynucleoside monophosphate molecules to the 3'-hydroxy end of the primer in a complex of primer and template, but this addition is in a template dependent manner. Generally, synthesis of extension products proceeds in the 5' to 3' direction of the newly synthesized strand until synthesis is terminated. Useful DNA polymerases include, for example, *E. coli* DNA polymerase I, T4 DNA polymerase, Klenow polymerase, reverse transcriptase and others known in the art. Preferably, the DNA polymerase is thermostable meaning that it is stable to heat and preferentially active at higher temperatures, especially the high temperatures used for specific priming and extension of DNA strands. More particularly, thermostable DNA polymerases are not substantially inactive at the high temperatures used in polymerase chain reactions as described herein. Such temperatures will vary depending on a number of reaction conditions, including pH, nucleotide composition, length of primers, salt concentration and other conditions known in the art.

A number of thermostable DNA polymerases have been reported in the art, including those mentioned in detail in U.S. Pat. No. 4,965,188 (Gelfand et al.) and U.S. Pat. No. 4,889,818 (Gelfand et al.), both incorporated herein by reference. Particularly useful polymerases are those obtained from various Thermus bacterial species, such as *Thermus aquaticus, Thermus thermophilus, Thermus filiformis*, and *Thermus flavus*. Other useful thermostable polymerases are obtained from various microbial sources including *Thermococcus literalis, Pyrococcus furiosus*, Thermotoga sp. and those described in WO-A-89/06691 (published Jul. 27, 1989). Some useful thermostable polymerases are commercially available, such as, AmpliTaq®, Tth, and UlTma® from Perkin Elmer, Pfu from Stratagene, and Vent and Deep-Vent from New England Biolabs. A number of techniques are also known for isolating naturally-occurring polymerases from organisms, and for producing genetically engineered enzymes using recombinant techniques.

A DNA polymerase cofactor refers to a nonprotein compound on which the enzyme depends for activity. Thus, the enzyme is catalytically inactive without the presence of cofactor. A number of materials are known cofactors including, but not limited to, manganese and magnesium salts, such as chlorides, sulfates, acetates and fatty acids salts. Magnesium chlorides and sulfates are preferred.

Also needed for PCR are two or more deoxyribonucleoside-5'-triphosphates, such as two or more of dATP, dCTP, dGTP, dTTP and dUTP. Analogues such as dITP and 7-deaza-dGTP are also useful. Preferably, the four common triphosphates (dATP, dCTP, dGTP and dTTP) are used together.

The PCR reagents described herein are provided and used in PCR in suitable concentrations to provide amplification of the target nucleic acid. The minimal amounts of primers, DNA polymerase, cofactors and deoxyribonucleoside-5'-triphosphates needed for amplification and suitable ranges of each are well known in the art. The minimal amount of DNA polymerase is generally at least about 0.5 units/100 $\mu$l of solution, with from about 2 to about 25 units/100 $\mu$l of solution being preferred, and from about 7 to about 20 units/100 $\mu$l of solution being more preferred. Other amounts may be useful for given amplification systems. A "unit" is defined herein as the amount of enzyme activity required to incorporate 10 nmoles of total nucleotides (dNTP's) into an extending nucleic acid chain in 30 minutes at 74° C. The minimal amount of each primer used in amplification is at least about 0.075 $\mu$molar with from about 0.1 to about 2 $\mu$molar being preferred, but other amounts are well known in the art. The cofactor is generally present in an amount of from about 2 to about 15 mmolar. The amount of each dNTP is generally from about 0.25 to about 3.5 mmolar.

The PCR reagents can be supplied individually, or in various combinations, or all in a buffered solution having a pH in the range of from about 7 to about 9, using any suitable buffer, many of which are known in the art.

Other reagents that can be used in PCR include, for example, antibodies specific for the thermostable DNA polymerase. Antibodies can be used to inhibit the polymerase prior to amplification. Antibodies useful in the present invention are specific for the thermostable DNA polymerase, inhibit the enzymatic activity of the DNA polymerase at temperatures below about 50° C., and are deactivated at higher temperatures. Useful antibodies include, monoclonal antibodies, polyclonal antibodies and antibody fragments. Preferably, the antibody is monoclonal. The antibodies useful in the present invention can be prepared using known methods such as those described in Harlow et al., Antibodies: A Laboratory Manual, Cold Spring Harbor, N.Y. (1988).

Representative monoclonal antibodies are described in U.S. Pat. No. 5,338,671 (Scalice et al.), the contents of which are hereby incorporated by reference. Two such monoclonal antibodies are readily obtained by a skilled artisan using conventional procedures, and starting materials including either of hybridoma cell lines HB 11126 or 11127, deposited with the American Type Culture Collection (ATCC) (Rockville, Md.). The monoclonal antibody is present in an amount of from about 5:1 to about 500:1 molar ratio to the DNA polymerase.

Amplified nucleic acids can be detected in a number of known ways, such as those described in U.S. Pat. No. 4,965,188 (Gelfand et al.). For example, the amplified nucleic acids can be detected using Southern blotting, dot blot techniques, or nonisotopic oligonucleotide capture detection with a labeled probe. Alternatively, amplification can be carried out using primers that are appropriately labeled, and the amplified primer extension products can be detected using procedures and equipment for detection of the label.

In a preferred embodiment, the amplified target nucleic acid is detected using an oligonucleotide probe that is labeled for detection and can be directly or indirectly hybridized with the amplified target. The probe may be soluble or attached to a solid support. In another preferred embodiment, one or more of the primers used to amplify the target nucleic acid is labeled, for example, with a specific binding moiety. The resulting primer extension product into which the labeled primer has been incorporated can be captured with a probe. Detection of the amplified target hybridized to the probe can be achieved by detecting the presence of the labeled probe or labeled amplified target using suitable detection equipment and procedures that are well known in the art. Certain labels may be visible to the eye without the use of detection equipment.

In a more preferred embodiment, one or more of the primers used to amplify the target nucleic acid is labeled with biotin and the biotinylated amplified target nucleic acids are hybridized to probes attached to a solid support. The bound targets are then detected by contacting them with a streptayidin-peroxidase conjugate in the presence of an oxidant, such as hydrogen peroxide, and a suitable dye-forming composition. For example, useful dye-providing reagents include tetramethylbenzidine and derivatives thereof, and leuco dyes, such as triarylimidazole leuco dyes as described in U.S. Pat. No. 4,089,747 (Bruschi).

As used herein, when in reference to time the term "about" refers to ±10% of that time limit. When used in reference to temperatures, the term "about" refers to ±5° C.

The following Examples are provided to illustrate certain embodiments of the present invention, and are not to be construed as limiting the invention.

EXAMPLES

Materials and Methods

Recombinant DNA polymerase from Thermus aquaticus was prepared using known procedures, such as that described in EP-A-0 482 714, and had an activity of about 250,000 units/mg of protein.

The primers and probes used in the following Examples were prepared using known starting materials and procedures using an Applied Biosystems Model 380B, three column DNA synthesizer using standard phosphoramidite chemistry and the ABI 1 $\mu$ molar scale, fast cycle protocol. Nucleoside-3'-phosphoramidites and nucleoside derivatized controlled pore glass supports were obtained from Applied Biosystems. The primers had the sequences identified above. They were functionalized at the 5' end with two amino tetraethylene glycol spacers according to U.S. Pat. 4,962,029, followed by a single commercially available DuPont biotin phosphoramidite. The probes were functionalized at the 3' end with two tetraethylene glycol spacers followed by a single aminodiol linking group according to U.S. Pat. No. 4,914,210. All purifications were carried out using a nucleic acid purification column. Deoxyribonucleotides (dNTP's) were obtained from Sigma Chemical Co.

In some experiments phosphorothioated primers were used. Phosphorothioated primers having phosphorothioate linkages in the ultimate and penultimate positions relative to the 3'-hydroxyl group were prepared by H-phosphate chemistry according to the method of U.S. Pat. No. 5,003,087, also described n the technical bulletin accompanying Cat. No. 40-4036-xx, Glen Research, Sterling, Va.

A streptayidin-peroxidase conjugate solution was used that comprised a commercially available (Sigma Chemical Co.) conjugate of streptayidin and horseradish peroxidase, casein (0.5%), and merthiolate (0.5%) in a phosphate buffered saline solution (24 mmolar sodium phosphate and 75 mmolar sodium chloride). 10 mmolar 4'-hydroxyacetanilide was added as a conjugate stabilizer.

The internal positive control (IPC) target was prepared as follows. The IPC sequence was generated as a single-stranded synthetic target by phosphoramidite oligonucleotide synthesis. It was then amplified with oligonucleotide primers containing 5' restriction sites and directionally cloned into the pBluescript II KS(–) plasmid vector. Large scale cultures of plasmid-containing *E. coli* were grown under ampicillin selection as previously described (Sambrook et al., Molecular Cloning: A Laboratory Manual. Cold Harbour Press 1989). Plasmid DNA was subsequently purified on Qiagen columns using the appropriate reagents from the vendor and following the vendor's procedure. The resulting purified plasmid was resuspended in TE buffer (10 mM Tris pH 8.0, 1 mM EDTA pH 8.0) and concentration was determined spectrophotometrically (Sambrook et al., 1989). The plasmid was subsequently digested with the restriction enzyme ScaI to linearize the plasmid while maintaining an intact target sequence. Serial dilutions of all targets were carried out in TE buffer with 10 mg/ml sonicated calf thymus DNA (Sigma).

The leuco dye dispersion contained agarose (0.5%), 4,5-bis(4-dimethylaminophenyl)-2-(4 hydroxy-3-methoxyphenyl)imidazole leucodye (250 $\mu$molar), diethylenetriamine pentaacetic acid (100 $\mu$molar), 3'-chloro-4'-hydroxyacetanilide (5 mmolar), polyvinylpyrrolidone (112 mmolar), and sodium phosphate, monobasic, 1-hydrate (10 mmolar) and hydrogen peroxide (H202)(8.82 mmolar).

The wash solution (pH 7.4) contained sodium chloride (373 mmolar), (ethylenedinitrilo)tetraacetic acid disodium salt (2.5 mmolar), decyl sodium sulfate (38 mmolar) and ethylcerithio salicylic acid, sodium salt (25 $\mu$molar) in sodium phosphate, monobasic 1-hydrate buffer (25 mmolar).

The polymerase chain reaction mixture (75 $\mu$l) contained tris(hydroxymethyl)aminomethane buffer (10–18 mmolar, pH 8), EDTA (0–0.75 mmolar) potassium chloride (50 mmolar), magnesium chloride (4 mmolar), dATP, dCTP, dGTP, and dTTP (0.3 mM each), the stated primers (0.4 $\mu$molar each unless otherwise noted), Type IV gelatin (100 mg/mL), Taq polymerase (16 units/100 $\mu$l), and glycerol (9.5%). A fifty fold molar excess (over polymerase) of TP1-12.2 and a 5×excess of TP4-9.2 were used.

To form capture reagents, the probes were covalently attached to polymeric particles (1 $\mu$m average diameter) prepared, using conventional emulsion polymerization techniques, from poly[styrene-co -3-(p-vinylbenzylthio) propionic acid] (95:5 to 98:2 weight ratio, 1 $\mu$m average diameter). A suspension of the particles in water was washed with 2-(N-morpholino)ethanesulfonic acid buffer (0.1 molar, pH 6), and suspended to about 10% solids. A sample (3.3 ml) of the washed particles, diluted to 3.33% solids in the buffer (0.1 molar, was mixed with 1-(3-dimethylaminopropyl)-3-ethylcarbodiimide hydrochloride (2.1 ml of 84 mg/ml water) and the probe (983 $\mu$l of 44.44 OD/ml nanopure water). The resulting suspension was heated at 50° C. in a water bath for about two hours with intermittent mixing and centrifuged. The particles were then washed three times with tris (hydroxymethyl)aminomethane buffer (0.01 molar, pH 8) containing (ethylenedinitrilo)tetraacetic acid disodium salt (0.0001 molar) and resuspended therein to 4% solids.

Upon dilution to 0.25% solids with buffer, the capture reagents (1–2 $\mu$l) were applied to and dried in defined regions of the microporous membranes (LOPRODYNE™ polamide membrane, 1.2 $\mu$m average pore size, from Pall Corp.) in the test wells of SURECELL™ disposable test devices (available from Johnson & Johnson Clinical Diagnostics, Inc.), which are described in detail in U.S. Pat. No. 4,948,561 (Hinckley et al).

Other reagents and materials were obtained either from commercial sources or prepared using readily available starting materials and conventional procedures.

Experiments

Primer Selection:

Applicants began development of their PCR amplification system for HIV-1 and HIV-2 by identifying highly conserved sequence regions of HIV-1. Primers were designed to conserved regions utilizing the following criteria: (1) product lengths could not exceed 200 nucleotides, as smaller products amplify at higher efficiency and are less sensitive to reductions in effective polymerase concentration, anneal/extend time or average size of prepared sample material, (2) primer sets must have a functional probe region between them for specific detection of amplified product, (3) mismatches near the 3' end of the primer would be far less preferable than mismatches near the 5' end and (4) the primers would need to pass established criteria for primer development in terms of 3' end stability, length, GC content and interactions with other potential primers and probes.

Initially, the following 11 primers were selected for testing:

```
GACCAGATCTGAGCCTGGGAGCT, 23-mer (SEQ ID NO. 1)

GACCAGATCTGAGCCTGGGAGCTC, 24-mer (SEQ ID NO. 23)

CTGCTTAAGCCTCAATAAAGCTTGCCTTGAG, 31-mer (SEQ ID NO. 24)

CTGCTTAAGCCTCAATAAAGCTTGCCTTGA, 30-mer (SEQ ID NO. 2)

GGTCTGAGGGATCTCTAGTTACCAGAGT, 28-mer (SEQ ID NO. 25)

GGGTCTGAGGGATCTCTAGTTACCAGAGT, 29-mer (SEQ ID NO. 3)

GGGTCTGAGGGATCTCTAGTTACCAG, 26-mer (SEQ ID NO. 26)

TGTTCGGGCGCCACTGCTAGAGA, 23-mer (SEQ ID NO. 4)

TCGGGTTTATTACAGGGACAGCAGAGA, 27-mer (SEQ ID NO. 7)

GTATTACTACTGCCCCTTCACCTTTCCA, 28-mer (SEQ ID NO. 27)

CTTGTATTACTACTGCCCCTTCACCTTTCCA, 31-mer (SEQ ID NO. 8)
```

Many of these primers are identical to 1 or 2 of the other primers except for the sequences at the 5' end of the primer, the 3' end of the primer or both. SEQ ID NOS. 1 and 23 represent one forward primer region of the LTR region of the HIV-1 genome, while SEQ ID NOS. 24 and 2 represent another LTR forward primer region. SEQ ID NOS. 25, 3, and 26 represent one LTR reverse primer region while SEQ ID NO. 4 represents a second region. SEQ ID NO. 7 was the sole forward primer designed for the POL region of the HIV-1 genome, while SEQ ID NOS. 27 and 8 are reverse primers which should be able to complement SEQ ID NO. 7.

These primers were tested by amplifying either 0 or 15 copies of HIV-1 target per 75 ml reaction by PCR for 40 cycles on the PE9600 Thermocycler, followed by detection via gel electrophoresis. HIV-1 target DNA was prepared as follows, 8E5 cells (Folks T. M., et al. J. Exp. Med. 164: 280, 1986), which contain a single copy of a polymerase deficient HIV-genome incorporated into the host chromosome were propagated in 90% RPMI media with 10% fetal bovine serum. DNA was prepared from $2.5 \times 10^9$ cells/1 liter of culture via typical SDS, Proteinase K digestion followed by phenol/chloroform extraction and ethanol precipitation. The resultant extract was banded over cesium chloride, dialyzed, extracted, precipitated with ethanol and resuspended in 10 mM Tris/1 mM EDTA (pH 8.0) for analysis. DNA content was calculated by optical density measurement at $A_{260}$. All reactions were carried out as described above except that 3 mg of calf thymus DNA was added per 75 µl reaction. Duplicate reactions were run for each of the 16 possible LTR combinations and 2 possible POL combinations. Gel results are shown in Table 1. The control reactions containing no HIV-1 target demonstrated a visible side product band for the SEQ ID NOS. 23/4 combination with an anneal/extend temperature of 68° C., making this combination a less preferable primer set. Aside from this side product, essentially no visible side products were observed at either anneal/extend temperature.

The selected primers were further compared in terms of gel band intensity at both anneal/extend temperatures. There was little difference in gel band intensity between combinations containing SEQ ID NOS. 1 or 23. SEQ ID NOS. 24 and 2 performed equivalently to each other when combined with different reverse primers. Out of the 3 overlapping reverse primers, SEQ ID NOS. 3 and 26 outperformed SEQ ID NO. 25, especially with anneal/extend temperatures of 70° C. All combinations which included SEQ ID NO. 4 amplified well at both anneal/extend temperatures. SEQ ID NO. 27 performed very poorly compared with SEQ ID NO. 8 (both in combination with SEQ ID NO. 1); therefore, no future testing was carried out with SEQ ID NO. 27.

TABLE 1

Screening of potential HIV-1 primer sets

| Primer Combination | 10 copy Product Intensity | | Zero Target |
|---|---|---|---|
| SEQ ID NOS. | 68° C. | 70° C. | Side Products |
| 1/25 | ++ | + | (−) |
| 1/3 | ++ | ++ | (−) |
| 1/26 | ++ | ++ | (−) |
| 1/4 | ++ | ++ | (−) |
| 23/25 | ++ | ++ | (−) |
| 23/3 | ++ | ++ | (−) |
| 23/26 | ++ | ++ | (−) |
| 23/4 | ++ | ++ | W |
| 24/25 | + | W+ | (−) |
| 24/3 | ++ | + | (−) |
| 24/26 | ++ | + | (−) |
| 24/4 | ++ | ++ | (−) |
| 2/25 | + | W | (−) |
| 2/3 | ++ | + | (−) |
| 2/26 | ++ | + | (−) |
| 2/4 | ++ | ++ | (−) |
| 7/27 | W− | (−) | (−) |
| 7/8 | + | W− | (−) |

Gel Band Intensity: ++ > + >W+ > W > W− > (−)

The next experiment was a co-amplification reaction of the SEQ ID NOS. 7/8 primer set and with all possible LTR primer sets individually. This coamplification was carried out in the presence of an internal positive control (IPC). Amplification was carried out using Johnson & Johnson Clinical Diagnostics' PCR analyzer, an automated PCR processor described in U.S. Pat. No. 5,089,233. HIV target was amplified for 40 cycles using three different thermal profiles:

(1) 95° C. denaturation for 15 seconds and 68 ° C. anneal/extend for 30 seconds;

(2) 95° C. denaturation for 15 seconds and 66 ° C. anneal/extend for 30 seconds; and (3) 96° C. denaturation for 5 seconds and 68° C. anneal/extend for 40 seconds.

The amplified product was detected as described above.

Profile 1 was considered the state of the art condition, the second profile was used to determine which primer combinations were prone to side product formation and the third profile was an attempt to make the amplification more robust (by increasing the anneal/extend time) without increasing the overall cycle time. All reactions were run with 10 copies each of HIV and IPC targets per 75 μl reaction.

Amplification was more robust with the third amplification profile, especially with primer sets which generate longer (>150 nucleotides) products. The results also demonstrated that SEQ ID NOS. 23, 24, and 4 all have a propensity to form side products. Therefore, SEQ ID NOS. 23 and 24 were dropped. Further experiments were carried out with SEQ ID NOS. 1, 2 and 3.

Next, the absolute sensitivity of two HIV-1 co-amplification systems (SEQ ID NOS. 1/3 or 2/3 co-amplified with SEQ ID NOS. 7/8) was tested. Reactions were run for 40 or 45 cycles (96° C. 5 sec; 68° C. 40 sec either plus or minus the IPC target and primers. HIV target levels of 10, 5, 2.5, 1, 0.5 and 0 were run in duplicate for all conditions tested.

While the system which contained SEQ ID NOS. 2/3 had less side products formed during amplification (especially at 45 cycles), both systems appeared able to consistently detect as few as 2.5 copies of HIV-1 target. In the presence of IPC, the SEQ ID NOS. 1/3 co-amplification systems amplified one or both of the HIV products in 2 out of 4 replicates at 1 copy and 1 out of 4 replicates at 0.5 copies. Under the same conditions, the SEQ ID NOS. 2/3 co-amplification systems amplified one or both of the HIV products in 3 out of 4 replicates at 1 copy and 4 out of 4 replicates at 0.5 copies. All control reactions containing no target sequences run in this experiment were visually negative.

Following the same criteria outlined for HIV-1, HIV-2 primers were selected for testing. One additional criterion considered when designing the HIV-2 primers was minimization of potential interactions with candidate primers for both HIV-1 and HIV-2. The initial set of HIV-2 primers tested is listed below:

```
CCGGGATAGTGCAGCAACAGCAACA (SEQ ID NO. 11)

CGGGATAGTGCAGCAACAGCAACAG (SEQ ID NO. 28)

CCCCAGACGGTCAGTCGCAACA (SEQ ID NO. 29)

CCCAGACGGTCAGTCGCAACA (SEQ ID NO. 12)

GGGAGGTTCTCTCCAGCACTAGCA (SEQ ID NO. 14)

CCCTGGGAGGTTCTCTCCAGCA (SEQ ID NO. 30)

GAGCCCTGGGAGGTTCTCTCCA (SEQ ID NO. 15)

GCGACTAGGAGAGATGGGAACACACA (SEQ ID NO. 16)

CTGTTCGGGCGCCAACCTGCTA (SEQ ID NO. 31)

CTGCACCTCAATTCTCTCTTTGGAAAAGACCAGTA (SEQ ID NO. 32)

GCACCTCAATTCTCTCTTTGGAAAAGACCAGTA (SEQ ID NO. 33)

TAGACACAGGGGCTGACGACTCAATAGT (SEQ ID NO. 18)

CACAGGGGCTGACGACTCAATAGTAGCA (SEQ ID NO. 19)

GCCAAAAATGTTGATTGGGGTATCTCCTGTCATTA (SEQ ID NO. 20)

GCCAAAAATGTTGATTGGGGTATCTCCTGTCA (SEQ ID NO. 34)
```

To prepare HIV-2 DNA, 10E8 cells infected with HIV-2, strain Hut78 NIH-Z, were treated with SDS and proteinase K followed by phenol/chloroform extraction and ethanol precipitation the resultant extract was resuspended in 10 mM TRIS/1 mM EDTA pH 8.0, for analysis.

Individual HIV-2 primers were screened for the ability to form side products with HIV-1 primers SEQ ID NOS. 1, 2, 3, 26, 4, 7, and 8 under two separate amplification profiles:
(1) 40 cycles with an anneal/extend temperature of 68° C., and
(2) 5 cycles with an anneal/extend temperature of 62° C. followed by 35 cycles with an anneal/extend temperature of 68 ° C. The second profile was chosen for testing to determine which primer sets could minimize side product formation under conditions that minimize the effects of target mismatches. Any primers which formed strong side products with SEQ ID NOS. 7 and 8 utilizing condition 1 were immediately discarded, as these primers are minimally required for the co-amplification assay. The only two primers which were discarded due to this criterion were SEQ ID NOS. 30 and 31. The rest of the primers were narrowed down based on a variety of criteria. SEQ ID NO. 20 was chosen over SEQ ID NO. 34 due to a much lower level of side products formed by SEQ ID NO. 20 with HIV-1 primers. SEQ ID NOS. 11 and 12 were chosen over SEQ ID NOS. 28 and 29 because the former produced less side products and also conformed better to established criteria. SEQ ID NOS. 32 and 33 were dropped due to relatively poor amplification with either SEQ ID NOS. 20 or 34 under amplification condition 2. The remaining HIV-2 primer sets (SEQ ID NOS. 11/12, 14/16, 15/16, 18/20 and 19/20) all amplify extremely well and give very visible gel bands at 10 copies of HIV-2 target per reaction in a system which includes the following primers: SEQ ID NOS. 2, 3, 7, and 8 (each 0.4 μm), IPC-Fl (0.2 gm) and IPC-R1 (0.2 μm). There is very little side product formation by any of these amplification systems when amplification condition 1 from above is employed. There is significant side product formation when amplification condition 2 is employed, but the specific products are still very visible on a gel.

Probe Selection:

When dealing with highly divergent genomes such as HIV-1 and HIV-2, it is often difficult to identify three regions that are conserved enough to allow for amplification of each region with two primers and detection of each region with a single oligonucleotide probe. In systems in which the product length needs to be minimized, this problem is exacerbated to the point of making the task impossible unless the stringency of probing is reduced to the point at which probe specificity may be compromised. To avoid this problem, Applicants have developed a system in which multiple probes are utilized to allow detection of all known sequence variants without compromising assay specificity.

In order to probe the product formed by SEQ ID NOS. 2 and 3, a probe must be fit into a region only 34 nucleotides in length. The most conserved sequence in this region is the sequence of the probe SEQ. ID NO. 5.

```
probe:    CAACAGACGGGCACACACTACT (SEQ ID NO. 5)
```

This sequence is highly conserved in the majority of HIV-1 isolates, with one or less nucleotide difference between the probe and this region of sequence in the isolates; however, there are several divergent sequences which have 2–5 mutations in this region. To maximize the ability to detect sequences in the future which have further diverged from these sequences, an additional probe was designed, SEQ ID NO. 6.

```
probe:  GAACAGATGGGCACACACTGCT (SEQ ID NO. 6)
```

In the case of HIV-1 POL, both probes utilized were modified to minimize the highest number and severity of mutations encountered, and to maximize the strength of the bonds that do form. In doing this, both probes designed are not identical to any known isolate sequences. In using two probes, the maximum number of mutations encountered with any known isolates was reduced from 5 to 3. In addition, most of the remaining mutations are positioned near one of the ends of the probes, thus reducing their effect on hybridization. The sequences of the HIV-1 POL probes are shown below:

```
AGCTTTGCTGGTCCTTTCCAAAGTGGG (SEQ ID NO. 9)
AGTTGTGCCGGTCCTTTCCAAATTGGG (SEQ ID NO. 10)
```

The aforementioned situation described is similar for the sequences selected in the HIV-2 POL system in that 2 probes were used. However, this situation is somewhat different in that the regions complementary to the two probes are overlapping but not identical in position. This is due to the fact that the sequence is divergent enough between the two subtypes of HIV-2 that one must modify the position of the probe in order to achieve the required thermal stability for each probe. With these two probes, all known HIV-2 sequences have no more than 2 nucleotide differences relative to their subtype-specific HIV-2 probe. The two HIV-2 POL probe sequences are shown below.

```
CCAAAAATAGTAGGGGAATAGGGGGATTC (SEQ ID NO. 21)
CACCCCAAAAATAGTAGGTGGGATAGGAGGG (SEQ ID NO. 22)
```

The co-amplification system described above was tested on HIV-1 and HIV-2 samples. The detection probes used for calorimetric detection were as follows:

```
HIV-1 LTR products:
    CAACAGACGGGCACACACTACT (SEQ ID NO. 5)
    GAACAGATGGGCACACACTGCT (SEQ ID NO. 6)
HIV-1 POL products:
    5'-AGCTTTGCTGGTCCTTTCCAAAGTGGG (SEQ ID NO. 9)
    5'-AGTTGTGCCGGTCCTTTCCAAATTGGG (SEQ ID NO. 10)
HIV-2 POL products:
    CCAAAAATAGTAGGGGAATAGGGGGATTC (SEQ ID NO. 21)
    CACCCCAAAAATAGTAGGTGGGATAGGAGGG (SEQ ID NO. 22)
HIV-2 LTR products:
    CCACGCTTGCTTGCTTAAAGACCTC (SEQ ID NO. 17)
HIV-2 ENV products:
    TGGACGTGGTCAAGAGACAACAAGAA (SEQ ID NO. 13)
```

Five culture amplified HIV-1 isolates were tested including prototypical group M and group O isolates. All the co-amplification systems tested included the SEQ ID NOS. 7/8 primer set and an internal positive control primer set as well as one of four HIV-1 LTR primer sets: SEQ ID NOS. 1/3, 1/4, 2/3, and 2/4. All HIV-1-specific primer sets detected all isolates tested. Serial dilution of the target DNAs demonstrated that the SEQ ID NOS. 2/3 and 2/4 primer sets were the most sensitive LTR primer sets. The SEQ ID NO. 2/4 primer set appeared most sensitive for the highly divergent group O isolates.

Two different culture-amplified HIV-2 isolates were also tested to assess the performance of various HIV-2 primer sets. All reactions included the SEQ ID NOS. 11/12 and the IPC-F1/R1 primer sets and one of 4 LTR- or POL-specific HIV-2 primer sets: SEQ ID NOS. 18/20, 19/20, 14/16, and 15/16. All primer sets resulted in amplification of both targets at the higher target levels tested. HIV-2 target dilution suggested that the LTR primer sets were the most sensitive.

Strain sensitivity of various co-amplification systems was further assessed by testing 15 culture-amplified HIV-1 group O isolates, 17 frozen patient cell pellets from HIV-1-infected African patients (which should contain a high level of sequence heterogeneity) and 12 culture-amplified HIV-2 isolates. All 15 group O isolates were detected by the SEQ ID NO. 7/8 primer set and by the LTR primer sets SEQ ID NOS. 1/4, 2/3, and 2/4; however, 3 of the isolates were missed by the SEQ ID NO. 1/3 primer set. In the case of the LTR system, several of the group O isolates were positive with only one of the two LTR probes, the probe which is most homologous to the group O and U isolates and to the chimpanzee virus HIV1-CPZgab. These results demonstrate the improvement observed through the use of two detection probes for a single target. In the case of the African patient cell pellets described above, all three HIV-1 systems (SEQ ID NOS. 2/3, 2/4, and 7/8) tested positively; however, the SEQ ID NO. 2/3 system appeared to be the most sensitive system in this experiment, while the SEQ ID NO. 7/8 set appeared to be the least sensitive, detecting only 1 out of 2 replicates at the highest level of target DNA tested.

One of the 12 culture-amplified HIV-2 isolates tested negative for all primer sets tested. This sample was also negative with the control primer set used in the lab, suggesting that there may have been no HIV-2 DNA in the sample (it is well known that some HIV-2 isolates do not culture well). The other 11 isolates were positive with the ENV primer set and both LTR primer sets. In contrast, the SEQ ID NOS. 18/20 and 19/20 sets missed 2 out of 11 and 1 out of 11 isolates.

While the foregoing invention has been described in some detail for purposes of clarity and understanding, it will be clear to one skilled in the art from a reading of this disclosure that various changes in form and detail can be made without departing from the true scope of the invention.

What is claimed:

1. A method for amplifying nucleic acids from human immunodeficiency virus type 1 (HIV-1) comprising contacting a sample suspected of containing HIV-1 nucleic acid with four different nucleoside triphosphates, a thermostable DNA polymerase, and at least four oligonucleotides, under conditions such that said HIV-1 nucleic acid is amplified,
  wherein four oligonucleotides of said at least four oligonucleotides are selected from the sets:
    (a) SEQ ID NOS.: 1, 3, 7, and 8;
    (b) SEQ ID NOS.: 1, 4, 7, and 8;
    (c) SEQ ID NOS.: 2, 3, 7, and 8; and
    (d) SEQ ID NOS.: 2, 4, 7, and 8.

2. The method according to claim 1 wherein five oligonucleotides of said at least four oligonucleotides are selected from the sets:
    (a) SEQ ID NOS.: 1, 2, 3, 7, and 8;
    (b) SEQ ID NOS.: 1, 2, 4, 7, and 8;
    (c) SEQ ID NOS.: 2, 3, 4, 7, and 8;
    (d) SEQ ID NOS.: 1, 3, 4, 7, and 8; and
    (e) SEQ ID NOS.: 1, 2, 3, 4, 7 and 8.

3. The method according to claim 2 wherein said five oligonucleotides are SEQ ID NOS.: 2, 3, 4, 7, and 8.

4. The method according to claim 1 wherein six oligonucleotides of said at least four oligonucleotides are SEQ ID NOS.: 1, 2, 3, 4, 7, and 8.

5. The method according to claim 1 wherein said thermostable DNA polymerase is selected from the sets: Thermus aquaticus polymerase, Thermus thermophilus polymerase, and Thermococcus litoralis polymerase.

6. A method for amplifying and detecting HIV-1 nucleic acid comprising:
    (i) contacting a sample suspected of containing HIV-1 nucleic acid with four different nucleoside triphosphates, a thermostable DNA polymerase, and at least four oligonucleotides, under conditions such that said HIV-1 nucleic acid is amplified,
      wherein four oligonucleotides of said at least four oligonucleotides are selected from the sets:
        (a) SEQ ID NOS.: 1, 3, 7, and 8;
        (b) SEQ ID NOS.: 1, 4, 7, and 8;
        (c) SEQ ID NOS.: 2, 3, 7, and 8; and
        (d) SEQ ID NOS.: 2, 4, 7, and 8;
    (ii) denaturing said amplified HIV-1 nucleic acid to form single stranded nucleic acids; and
    (iii) detecting the presence or absence of said amplified HIV-1 nucleic acid.

7. The method according to claim 6 wherein said detection is accomplished using at least two oligonucleotide probes selected from the sets:
    (a) SEQ ID NOS.: 5 and 9;
    (b) SEQ ID NOS.: 5 and 10;
    (c) SEQ ID NOS.: 6 and 9; and
    (d) SEQ ID NOS.: 6 and 10.

8. The method according to claim 6 wherein said detection is accomplished using four oligonucleotide probes corresponding to SEQ ID NOS.: 5, 6, 9, and 10.

9. The method according to claim 6 wherein said detection is accomplished using a probe which is labeled or capable of being labeled with an enzyme.

10. A diagnostic kit useful for amplification of HIV-1 nucleic acid, said kit comprising:
    (i) oligonucleotides corresponding to SEQ ID NOS.: 1, 2, 3, 4, 7, and 8; and
    (ii) a thermostable DNA polymerase.

11. The diagnostic kit according to claim 10, which further comprises oligonucleotides corresponding to SEQ ID NOS: 5, 6, 9 and 10.

12. A method for amplifying nucleic acids of human immunodeficiency virus type 2 (HIV-2) comprising contacting a sample suspected of containing HIV-2 nucleic acid with four different nucleoside triphosphates, a thermostable DNA polymerase, and at least four oligonucleotides, under conditions such that said HIV-2 nucleic acid is amplified, wherein four oligonucleotides of said at least four oligonucleotides are selected from the sets:
(a) SEQ ID NOS.: 11, 12, 14, and 16;
(b) SEQ ID NOS.: 11, 12, 15, and 16;
(c) SEQ ID NOS.: 11, 12, 18, and 20;
(d) SEQ ID NOS.: 11, 12, 19, and 20;
(e) SEQ ID NOS.: 14, 16, 18, and 20;
(f) SEQ ID NOS.: 14, 16, 19, and 20;
(g) SEQ ID NOS.: 15, 16, 18, and 20; and
(h) SEQ ID NOS.: 15, 16, 19, and 20.

13. A composition comprising one or more of the following oligonucleotides:

```
GACCAGATCTGAGCCTGGGAGCT (SEQ ID NO. 1)

CTGCTTAAGCCTCAATAAAGCTTGCCTTGA (SEQ ID NO. 2)

GGGTCTGAGGGATCTCTAGTTACCAGAGT (SEQ ID NO. 3)

TGTTCGGGCGCCACTGCTAGAGA (SEQ ID NO. 4)

CAACAGACGGGCACACACTACT (SEQ ID NO. 5)

GAACAGATGGGCACACACTGCT (SEQ ID NO. 6)

TCGGGTTTATTACAGGGACAGCAGAGA (SEQ ID NO. 7)

CTTGTATTACTACTGCCCCTTCACCTTTCCA (SEQ ID NO. 8)

AGCTTTGCTGGTCCTTTCCAAAGTGGG (SEQ ID NO. 9)

AGTTGTGCCGGTCCTTTCCAAATTGGG (SEQ ID NO. 10)

CCGGGATAGTGCAGCAACAGCAACA (SEQ ID NO. 11)

CCCAGACGGTCAGTCGCAACA (SEQ ID NO. 12)

TGGACGTGGTCAAGAGACAACAAGAA (SEQ ID NO. 13)

GGGAGGTTCTCTCCAGCACTAGCA (SEQ ID NO. 14)

GAGCCCTGGGAGGTTCTCTCCA (SEQ ID NO. 15)

GCGACTAGGAGAGATGGGAACACACA (SEQ ID NO. 16)

TAGACACAGGGGCTGACGACTCAATAGT (SEQ ID NO. 18)

CACAGGGGCTGACGACTCAATAGTAGCA (SEQ ID NO. 19)

GCCAAAAATGTTGATTGGGGTATCTCCTGTCATTA (SEQ ID NO. 20)

CCAAAAATAGTAGGGGAATAGGGGGATTC (SEQ ID NO. 21)

CACCCCAAAAATAGTAGGTGGGATAGGAGGG (SEQ ID NO. 22).
```

14. A method for coamplifying HIV-1 and HIV-2 nucleic acid comprising contacting a sample suspected of containing HIV-1 or HIV-2 nucleic acid with four different nucleoside triphosphates, a thermostable DNA polymerase, SEQ ID NO. 7 and 8, at least one primer pair selected from SEQ ID NOS. 1, 2, 3, and 4, and at least one primer pair selected from SEQ ID NOS. 11, 12, 14, 15, 16, 18, 19 and 20, under conditions such that said HIV-1 or HIV-2 nucleic acid is amplified.

* * * * *